(12) United States Patent
Jung et al.

(10) Patent No.: US 11,484,721 B2
(45) Date of Patent: Nov. 1, 2022

(54) CONTACTING METHOD AND SYSTEM

(71) Applicant: Heraeus Deutschland GmbH & Co. KG, Hanau (DE)

(72) Inventors: Markus Jung, Hanau (DE); Thorsten Kaiser, Hanau (DE); Ashkan Hasiri, Hanau (DE); Katharina Musiol, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 98 days.

(21) Appl. No.: 16/710,298

(22) Filed: Dec. 11, 2019

(65) Prior Publication Data

US 2020/0188679 A1    Jun. 18, 2020

(30) Foreign Application Priority Data

Dec. 13, 2018   (DE) .................... 10 2018 221 635.5

(51) Int. Cl.
*A61N 1/375* (2006.01)
*A61N 1/362* (2006.01)
*H01B 7/02* (2006.01)

(52) U.S. Cl.
CPC .......... *A61N 1/3752* (2013.01); *A61N 1/362* (2013.01); *A61N 1/37512* (2017.08); *A61B 2562/227* (2013.01); *H01B 7/02* (2013.01)

(58) Field of Classification Search
CPC .. A61N 1/3752; A61N 1/37512; A61N 1/362; A61N 1/0472; A61N 1/048; A61N 1/0488; A61B 2562/227; H01B 7/02
See application file for complete search history.

(56) References Cited

U.S. PATENT DOCUMENTS

| 3,057,356 | A  | * | 10/1962 | Greatbatch | ............ A61N 1/362 607/9 |
| 3,154,067 | A  | * | 10/1964 | Stenstrom | .......... A61B 5/02444 600/500 |
| 7,364,479 | B1 |   | 4/2008  | Deily | |
| 9,757,555 | B2 | * | 9/2017  | Novotny | ........... B29C 45/14622 |
| 2003/0153952 | A1 | * | 8/2003  | Auricchio | ............ A61N 1/3684 607/9 |
| 2003/0236562 | A1 |   | 12/2003 | Kuzma | |
| 2004/0230268 | A1 | * | 11/2004 | Huff | ....................... A61N 1/056 607/116 |
| 2007/0168004 | A1 |   | 7/2007  | Walter | |
| 2009/0276021 | A1 |   | 11/2009 | Meadows et al. | |

(Continued)

*Primary Examiner* — Tammie K Marlen
(74) *Attorney, Agent, or Firm* — Dicke, Billig & Czaja, PLLC (57) ABSTRACT

One aspect is a system for reception or emission of an electrical signal from or into the human or animal body, comprising at least one insulated electrical conductor; a sleeve-shaped electrode that is electrically connected to the electrical conductor and includes an internal side, an external side, and a channel, wherein the channel defines a longitudinal axis along which the conductor is arranged. According to one embodiment, the conductor extends without interruption along the entire area of the electrode, and the electrode further includes a slit that extends from the internal side to the external side of the electrode and in which the conductor is appropriately arranged in the slit such that the electrode forms a direct durable mechanical and electrical connection to the conductor.

14 Claims, 3 Drawing Sheets

(56) References Cited

U.S. PATENT DOCUMENTS

| | | |
|---|---|---|
| 2011/0218603 A1 | 9/2011 | Victorine et al. |
| 2013/0338745 A1 | 12/2013 | Ollivier et al. |
| 2014/0052229 A1 | 2/2014 | Meadows et al. |
| 2014/0067035 A1 | 3/2014 | Barker |
| 2014/0296951 A1 | 10/2014 | Vetter et al. |
| 2014/0303702 A1 | 10/2014 | Jadwizak et al. |
| 2016/0208114 A1 | 7/2016 | Hendricks et al. |
| 2016/0303366 A1 | 10/2016 | Childers et al. |
| 2017/0182310 A1 | 6/2017 | Troetzschel et al. |
| 2017/0182311 A1 | 6/2017 | Keitel et al. |

* cited by examiner

CONTACTING METHOD AND SYSTEM

CROSS-REFERENCE TO RELATED APPLICATION

This Utility Patent Application claims priority to German Application No. 10 2018 221 635.5 filed on Dec. 13, 2018, which is incorporated herein by reference. This Utility Patent Application is related to co-pending U.S. Ser. No. 16/708,750, entitled "CONTACTING METHOD AND SYSTEM" filed Dec. 10, 2019.

TECHNICAL FIELD

One embodiment relates to a system for reception or emission of an electrical signal from or into the human or animal body, comprising at least one insulated electrical conductor, an electrically connected electrode, and a channel, whereby the channel defines a longitudinal axis along which the conductor is arranged. Moreover, one embodiment relates to a method for contacting an electrical conductor.

BACKGROUND

The electrical contacting of an electrical conductor can often be a major challenge, in particular if dimensions are small. In this context, for example, good electrical conductivity and mechanical stability even upon exposure to strong loads over an extended period of time are desired. This applies in particular to the electrical contacting of lines in medical devices. Referring to devices that are introduced into the human or animal body, it is desirable to use thin lines although these may be a challenge in terms of the electrical contacting due to their size. Another very important feature is the reliability of medical devices such as, for example, cardiac pacemakers, implantable cardioverters, defibrillation devices, and cardiac resynchronisation devices, particularly with a view to keeping the material fatigue as low as possible. In particular the line and the electrical connectors are exposed to strong loads in operation.

Since invasive surgery is commonly required in order to introduce medical devices into the body or to remove or replace parts thereof, the individual components of the device are therefore desired to have a long service life in order to reduce the need for surgical interventions.

EP3185248A1 describes a method for electrically contacting of a coated line to a particle. For this purpose, the insulation is partially removed and electrically conductive particles are introduced into a window (Via) generated in the process. The particle forms a conductive connection between the conductor and a ring electrode surrounding the conductor. In the process, creepage of the plastic insulation may lead to a loss of contact between the line and the particle though.

U.S. Pat. No. 7,364,479 describes a contacting method that is comparatively resource-consuming.

US2016303366A1 describes the contacting that uses an additional connecting piece and therefore is resource-consuming as well.

US20130338745A1 describes a contacting by means of micro-slide. This is resource-consuming and can lead to an instability of the contact in practical application due to the manufacturing tolerances.

US20130338745 describes a contacting by means of ring electrodes, which include multiple hollow spaces for the electrical conductor. This method is resource-consuming and not very flexible.

In conventional methods it is often not possible to connect, especially, small structures of conductors and electrodes by means of a firmly-bonded connection, for example a welded connection, without damaging the plastic insulation of the conductor more than necessary. The connection of a conventional welded connection at the end of the electrode is susceptible to fatigue fracturing. Conventional crimp methods often destroy the surface structure of the electrode.

SUMMARY

It is the object of the present embodiment to overcome the illustrated and further disadvantages of the prior art. For example, one embodiment provides an improved and simplified method for the electrical contacting of an electrode to a conductor that is advantageous especially in the micrometer range. The method is simpler and more flexible than methods of the prior art and delivers products with improved properties, as shall be illustrated in the following. Moreover, a system with an improved contacting between an electrical conductor and an electrode is provided. The improved contacting may be expressed, for example, in higher reliability, stability, and conductivity. In particular, one embodiment delivers a contacting with improved breaking strength and fatigue stability.

The objects are solved by the methods and systems described herein, in particular those that are described in the patent claims.

One embodiment is a system for reception or emission of an electrical signal from or into the human or animal body, including at least one insulated electrical conductor; a sleeve-shaped electrode that is electrically connected to the electrical conductor and comprises an internal side, an external side, and a channel. The channel defines a longitudinal axis along which the conductor is arranged. The conductor extends without interruption along the entire area of the electrode, and the electrode further comprises a slit that extends from the internal side to the external side of the electrode and in which the conductor is appropriately arranged in the slit such that the electrode forms a direct durable mechanical and electrical connection to the conductor.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIGS. 3A, 3B, 3C illustrate steps of a method according to one embodiment:

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Referring to the embodiments described herein, whose elements "comprise" a certain feature (for example a material), a further embodiment shall also be considered as a matter of principle, in which the corresponding element consists of the feature alone, i.e. does not include any further components.

In as far as an element is referred to in the singular form in an embodiment, an embodiment, in which multiple of the elements are present, shall be considered as well.

Unless specified otherwise or clearly excluded by the context, it shall be possible as a matter of principle and shall herewith be taking into consideration unambiguously that features of different embodiments can also be present in other embodiments described herein. Moreover, it is considered, as a matter of principle, that all features described herein with reference to a method shall also be applicable to the products and devices described herein. Only for reasons of brevity, all of these considered combinations are not specified explicitly in all cases. Moreover, technical solutions known to be equivalent to the features described herein shall be included by the scope of embodiments as a matter of principle.

A first aspect of one embodiment relates to a system for reception or emission of an electrical signal from or into the human or animal body, comprising at least one insulated electrical conductor, a sleeve-shaped electrode that is electrically connected to the electrical conductor and includes an internal side, an external side, and a channel, whereby the channel defines a longitudinal axis along which the conductor is arranged; whereby the conductor extends without interruption along the entire area of the electrode, and the electrode further includes a slit that extends from the internal side to the external side of the electrode and in which the conductor is appropriately arranged in the slit such that the electrode forms a direct durable mechanical and electrical connection to the conductor.

In one embodiment, the system is set up for reception of an electrical signal from the human or animal body. In one embodiment, the system is set up for emission of an electrical signal to the human or animal body. In one embodiment, the system is set up for both reception of an electrical signal from the human or animal body and for emission of an electrical signal to the human or animal body.

Electrical Conductor

The electrical conductor can, for example, be an insulated metal wire. Accordingly, the conductor can include a metal wire and an insulation or consist of one or more metal wires and an insulation. In some embodiments, the conductor includes one or more of the metals Pt, Ir, Ta, Pd, Ti, Fe, Au, Mo, Nb, W, Ni, Ti, or a mixture and/or alloy thereof. In some embodiments, the conductor includes the alloys MP35, PtIr10, PtIr20, 316L, 301 or nitinol. The conductor can just as well include multilayered material systems. In some embodiments, the electrically conductive part of the conductor consists of one or more of the materials and an insulation. Suitable insulations are described in more detail in the following. In one embodiment, the conductor includes MP35, Au, Ta, Pt, Ir or Pd. In some embodiments, the electrically conductive part of the conductor consists of MP35, Au, Ta, Pt, Ir or Pd or alloys of the metals. In some embodiments, the conductor contains less than 3%, 2% or less than 1% Fe.

MP35 is a nickel-cobalt-based hardenable alloy. A variant of MP35 is described in the industrial standard ASTM F562-13. In one embodiment, MP35 is an alloy that includes 33 to 37% Co, 19 to 21% Cr, 9 to 11% Mo, and 33 to 37% Ni.

PtIr10 is an alloy made of 88 to 92% platinum and 8 to 12% iridium.

PtIr20 is an alloy made of 78 to 82% platinum and 18 to 22% iridium.

316L is an acid-resistant, CrNiMo austenitic steel with approx. 17% Cr; approx. 12% Ni and at least 2.0% Mo. One variant of 316L is described in the industrial standard DIN EN10088-2. In one embodiment, 316L is an alloy that includes 16.5 to 18.5% Cr, 2 to 2.5% Mo, and 10 to 13% Ni.

301 is a chromium-nickel steel with high corrosion resistance. One variant of 301 is described in the industrial standard DIN 1.4310. In one embodiment, 301 is an alloy that includes 16 to 18% Cr and 6 to 8% Ni.

Nitinol is a nickel-titanium alloy with a shape memory with an ordered-cubic crystal structure and a nickel fraction of approximately 55%, whereby titanium accounts for the remaining fraction. Nitinol has good properties with regard to biocompatibility and corrosion resistance.

Unless specified otherwise, all percentages given herein shall be understood to be mass percentages (weight %).

The electrical conductor is electrically insulated. In as far as multiple electrical conductors are present, these include no electrical connection to each other. In some embodiments, the conductor includes a dielectric sheathing, for example made of an electrically insulating plastic material, silicone or rubber. Suitable plastic insulations include, for example, polyethylene, polyurethane, polyimide, polyamide, PEEK, and fluorinated plastics such as, for example, ETFE, PTFE, PFA, PVDF or FEP. In one embodiment, the insulation of the conductor includes an exposed section in the area of the electrode. The conductive part of the conductor is accessible at this exposed section such that it can be connected to the electrode.

Multiple Conductors can be Arranged into a Conductor Bundle.

The conductor extends without interruption along the entire area of the electrode. Therefore, the conductor is connected to the electrode without requiring the conductor to be severed. In one embodiment, the conductor includes no free end in the area of the electrode for connecting the conductor to the electrode. In one embodiment, the conductor extends along the entire length of the electrode without interruption or without a free end. In one embodiment, the conductor extends along the entire length of the channel of the electrode without interruption or without a free end. In one embodiment, the conductor extends along the entire length of the slit without interruption or without a free end.

Electrode

The electrode is a conductive, hollow and electrically conductive element, which can be attached appropriately as a sleeve to one or more conductors such that it surrounds the conductor or conductors or conductor bundle. In one embodiment, the channel surrounds all conductors of the system. The electrode can in one embodiment take the shape of a hollow cylinder or a similar shape. The electrodes are also referred to as "ring electrodes". However, other electrode geometries that can be connected to an electrical conductor by means of the method described herein are feasible just as well.

The electrode includes a channel and the conductor is arranged along the longitudinal axis thereof. In one embodiment, the conductor is arranged in the channel. The slit is understood to be a part of the channel in this context.

The electrode includes a first external edge and a second external edge that are arranged in the area of the two openings of the channel. Accordingly, the first external edge and the second external edge are arranged on opposite sides of the electrode.

In some embodiments, the electrode includes one or more of the metals Pt, Ir, Ta, Pd, Ti, Fe, Au, Mo, Nb, W, Ni, Ti, or a mixture and/or alloy thereof. In some embodiments, the electrode includes the alloys MP35, PtIr20, PtIr10, PdIr10, 316L, or 301. The electrode can just as well include multi-layered material systems. In some embodiments, the electrode consists of one or more of the materials.

The electrode has an internal side that faces the part of the conductor that is guided in the channel, and an external side that faces away from the part of conductor that is guided in the channel.

In some embodiments, the electrode has an external diameter of less than 1.5 mm, in a specific embodiment it has an external diameter of less than 0.8 mm.

Slit

The electrode includes a slit that extends from the internal side to the external side of the electrode. The slits can extend continuously from the internal side to the external side of the electrode. A little of this type is formed by partial or complete severing of the jacket of the electrode. This means that the slit is a partial or complete interruption of the electrode wall. The slit serves for connecting the electrode to the conductor, as is illustrated in more detail below. In one embodiment, the slit includes two surfaces opposite from each other which are set up to establish a direct force-locking and/or firmly-bonded electrically conductive connection of the conductor to the electrode.

In the scope of one embodiment, the slit shall be called a "slit" even if parts of the electrode in this area touch each other after the slit has been pressed together and/or welded for contacting the conductor, and thus have been closed again fully or partially. Accordingly, a slit does not necessarily have to be characterised by a permanently existing gap between different parts of the electrodes. A re-closed connection of parts of the electrode, which was recognisably separated at an earlier time, in particular prior to the contacting of the electrode, shall be referred to as a slit in the scope of one embodiment.

In some embodiments, the slit extends continuously along the longitudinal axis of the channel from a first external edge of the electrode, on the electrode side of which the conductor is guided into the channel, to a second external edge of the electrode, on the electrode side of which the conductor is guided again out of the channel. This means that the slit extends on one side of the electrode from edge to edge along the entire jacket surface of the electrode. In other embodiments, the slit only touches the first external edge, only the second external edge or neither. In some embodiments, the material of the electrode surrounds the slit completed. Accordingly, the slit can just as well be arranged exclusively within the jacket surface of the electrode without touching one of the external edges of the electrode.

The electrode can include, each on the first external edge of the electrode and on the second external edge of the electrode, a direct connection of the surfaces of the slit. A connection of this type arises, for example, in various embodiments of the method according to one embodiment that is described in more detail below: If, for example, the electrode is pushed together on the first external edge and the second external edge in order to connect the wire to the electrode, in particular in the centre part of the gap, in force-locking manner, the opposite surfaces of the slit can move toward each other until they touch exclusively on the first external edge and the second external edge of the electrode. In this context, it can be advantageous in one embodiment for the slits to include an essentially elliptical recess that is arranged in the centre of the slit and is set up to form a direct force-locking and/or firmly-bonded connection between the wire and the electrode. The embodiment is advantageous, for example, when the length of the electrode is much longer than the length required for contacting the conductor. In one embodiment, the length of the slit is smaller than the length of the electrode. The "length of the electrode" shall be understood to be the shortest distance between the first external edge and the second external edge of the electrode.

The slit is preferred to extend parallel or essentially parallel with respect to the longitudinal axis of the channel. If a conductor includes multiple wires, these can be stranded to each other such that the wires, in places, are arranged at an angle with respect to the longitudinal axis of the channel, for example in coil-shaped manner, although the conductor overall is arranged parallel with respect to the longitudinal axis of the channel. In this case, it can be advantageous in one embodiment to have the slit arranged parallel or essentially parallel with respect to a wire of the conductor.

The slit includes two edges that face each other. The edges can extend parallel with respect to each other throughout such that they include an even distance from each other. In one embodiment, the edges on the first or second external edge of the electrode are situated at a smaller distance from each other than in the central part of the slit. In one embodiment, the edges on the first and second external edge of the electrode are situated at a smaller distance from each other than in the central part of the slit. In one embodiment, the slit includes an essentially elliptical shape. In one embodiment, the slit includes an essentially elliptical recess that is arranged in the centre of the slit and is set up to form a direct force-locking and/or firmly-bonded connection between the conductor and the electrode. In one embodiment, the electrode includes, each on the first external edge of the electrode and on the second external edge of the electrode, a direct connection of the surfaces of the slit.

In one embodiment, the slit extends along the longitudinal axis of the channel from the first external edge of the electrode to the second external edge of the electrode such that the electrode is severed fully by the slit on one side.

In one embodiment, the electrode includes at least one further slit, for example a total of 2, 3, 4, 5 or 6 slits.

Connection of the Electrode to the Conductor

The conductor is arranged appropriately in the slit such that the electrode forms a direct, durable mechanical and electrical connection to the conductor. This is also illustrated in more detail below in the context of the method according to one embodiment. The conductor can be connected to the electrode inside the slit directly in force-locking and/or directly in firmly-bonded manner. For this purpose, the conductor is arranged between the internal surfaces of the slit.

A firmly-bonded connection can be attained, for example, by welding, brazing or soft soldering. In one embodiment, the firmly-bonded connection is a welded connection. The welded connection can be attained, for example, by laser welding. The melting of the conductor in the course of welding can be used to completely close the slit. By this means, the ingress of liquids or other contaminations into the slit can be prevented. Moreover, sharp edges or burrs on the external side of the electrodes can be covered and therefore smoothed. As mentioned earlier, a slit closed in this manner shall still be understood to be a "slit" in the sense of one embodiment since it is obvious to a person skilled in the art that the conductor was arranged and, for example, welded in a slit at the respective site.

In one embodiment, the electrical conductor is connected to the electrode inside the slit in a direct force-locking manner. The force-locking connection can be achieved by clamping, for example with pliers or another tool, crimping or swaging (drop forging) or other mechanical pressing methods known in this field. Several suitable methods are described in EP3185248A1. Further comparable methods known in this context to a person skilled in the art can be used as well.

In one embodiment, the electrical conductor is connected to the electrode inside the slit in a direct firmly-bonded manner. In one embodiment, the electrical conductor is connected to the electrode inside the slit in a direct force-locking manner. In one embodiment, the electrical conductor is connected to the electrode inside the slit in a direct firmly-bonded as well as a direct force-locking manner. In one embodiment, the electrical conductor is connected to the electrode inside the slit in a direct firmly-bonded manner, but not in a force-locking manner.

Moreover, the electrical conductor can just as well be connected to the electrode within the slit in a form-fitting manner.

In one embodiment, the electrical conductor is connected to the electrode in a firmly-bonded manner, but not in a force-locking manner. The electrical conductor can just as well be connected to the electrode exclusively in a firmly-bonded manner. A firmly-bonded connection is preferred to be a welded connection. Having an exclusively firmly-bonded connection allows a deformation of the electrode to be prevented and simultaneously attains a very stable, durable and very conductive connection between the conductor and the electrode. This is of particular advantage if the electrode includes a certain surface structure and shall still maintain such structure after the contacting to the conductor. For example, particularly smooth electrode surfaces with a precisely defined geometry can be attained by this means.

In some embodiments, the electrode is micro-structured, i.e. it includes further surface structures in addition to the slit and the connections mentioned above. The surface structures can impart a higher and precisely defined roughness to the electrode surface. The surface structures can be generated even before connecting the electrode to the conductor as they are not affected by a purely force-locking connection. This results in improved production procedures since a multitude of electrodes can be produced jointly from a metal tube, as shall be described in more detail herein. The metal tube can be structured and/or coated appropriately such that multiple structured and/or coated electrodes can be produced from the tube. It is also feasible to structure the electrode after attaching it to the conductor.

Similarly, it is feasible to use coated electrodes. According to the method according to one embodiment, in particular if the connection is of an exclusively firmly-bonded manner, a coating of this type is not affected by the inventive contacting of conductor to electrode. Moreover, the inventive connection (contacting) of the conductor within the slit favours the fatigue behaviour of the connection effectively increasing the long-term stability of the connection.

In one embodiment, the system includes a multitude of electrical conductors that are each insulated with respect to each other and are arranged in the channel along the longitudinal axis, whereby the electrode surrounds multiple or all of the conductors.

In one embodiment, the system includes a multitude of conductors and a multitude of electrodes, which each are electrically connected to exactly one other of the electrical conductors in the way described herein, such that the electrodes can be electrically addressed independent of each other. This means that each of the multitude of electrodes is set up to receive an electrical signal exclusively from exactly one conductor or to emit an electrical signal to the conductor, but not to any of the other conductors. Accordingly, each electrode can be electrically triggered independent of the other electrodes.

In one embodiment, other than the direct connection between the conductor and the electrode, there is no further component present that connects the electrical conductor to the electrode in order to establish an electrical and mechanical connection in between. According to one embodiment, a welded or soldered connection or a material forming a connection of this type shall not be understood to be a "component" in this context. A component of this type could, for example, be an additional loop or an additional crimp element such as, for example, an additional sleeve, which is attached to the wire in order to subsequently connect it to the electrode. There being no need for a component of this type renders the contacting of the conductor to the electrode simpler and less error-prone.

Medical Device

In a further aspect, one embodiment provides an electrical medical device, comprising a system according to any one of the preceding aspects and embodiments thereof.

The electrical medical device can, for example, be a lead, pulse generator, cardiac pacemaker, cardiac resynchronisation device, sensor or stimulator. Leads are electrical lines that can be used, for example, in medical application such as neuromodulation, heart stimulation, deep brain stimulation, spinal cord stimulation or gastric stimulation. In one embodiment, the lead is set up and/or intended to be connected to a generator of an active implantable device. A lead of one embodiment can just as well be used in a medical device for reception of an electrical signal. A stimulator is a medical device that can achieve a physiological effect by emitting an electrical signal to the body of a living being. For example, a neurostimulator can effect an electrical signal in a nerve cell (for example an action potential) by emitting an electrical signal to the nerve cell.

A further embodiment relates to a micro-electrode or a micro-electrode array that includes a system described herein.

Method

A further aspect of one embodiment relates to a method for electrical contacting of an electrical conductor, comprising the following steps:
a. Providing an insulated electrical conductor and a sleeve-shaped electrode that includes an internal side, an external side, a channel, and a slit that extends from the internal side to the external side of the electrode;
b. exposing the insulation in a section of the conductor at which the conductor is to be connected to the electrode;
c. attaching the electrode to the conductor such that the conductor becomes arranged along the longitudinal axis thereof;
d. arranging the conductor in the slit such that the conductor can be connected to the electrode;
e. connecting the conductor to the electrode, whereby a direct force-locking and/or firmly-bonded electrical connection between the conductor and the electrode is formed within the slit.

In one embodiment, the slit extends continuously from the internal side to the external side of the electrode, as has already been illustrated above for the first aspect of one embodiment. In one embodiment, a rectangular area of the insulation of the conductor is removed. This can take place, for example, by laser ablation or similar methods. The width and the length of the exposed section determine how far a wire can be lifted out of the exposed section. Accordingly, the size of the exposed section needs to be selected appropriately such that the wire can be lifted sufficiently to be guided into the area of the slit. This depends on the diameter of the conductor and the wall thickness of the electrode. In this context, the width of the exposed surface can in one embodiment be equal to 0.5 to 2 times the conductor diameter and the length of the ablation can be equal to 2 to 8 times the wall thickness of the electrode. In a further embodiment, the width of the ablation surface is equal to 1 to 1.5 times the diameter of the conductor (including the insulation) and the length of the ablation is equal to 2 to 4 times the wall thickness of the electrode. The ablation surface is preferred to be essentially rectangular in shape. In one embodiment, the width is defined transverse to the longitudinal axis of the conductor at the place of the exposed insulation and the length is defined parallel to the longitudinal axis of the conductor. In one embodiment, the width is defined transverse to the longitudinal axis of a wire of the conductor at the place of the exposed insulation and the length is defined parallel to the longitudinal axis of the wire. In one embodiment, the length exceeds the width of the exposed surface.

After a part of the insulation of the conductor has been exposed, a wire is lifted from this section in order to guide it out of the conductor. Accordingly, the wire continues to be a component of the conductor, but projects from the remaining part of the conductor in the form of a loop. For example, the wire can be appropriately guided out of the conductor with a needle or another tool such that it extends beyond the insulation. Just as well, multiple wires, for example the entire conductive part of the conductor, can be guided out of the conductor. As a result, the wires, for example the entire conductive part of the conductor, extend beyond the installation of the conductor in the exposed section.

Subsequently, an electrode is slid onto the conductor such that the slit of the electrode is situated in the area of the lifted wire. The wire is being arranged appropriately such that it is situated between the surfaces of the slit. Subsequently, the conductor can be connected to the electrode by means of a force-locking and/or firmly-bonded connection. For example, the electrode can be pinched together such that the slit closes and clamps the wire between the surfaces of the slit. The wire can just a well be welded between the surfaces of the slit. It is also feasible to first clamp the wire in the slit and then weld it. Moreover, an additional material can be used in addition in order to close the gap. Various force-locking and form-fitting methods can be used to connect the wire to the electrode within the slit. For example, the conductor can initially be crimped to the electrode and then welded. It is also feasible to first clamp the conductor in the slit by mechanical pressure, for example exerted by means of pliers, and then to weld it. The conductor can also be connected by means of a tight fit of conductor and slit, whereby a mechanical contact between conductor and electrode is established. Subsequently, the wire can be welded to the electrode.

The steps of the method can be implemented in the order given or in any different order. For example, step c can just as well be performed before step b.

In one embodiment, the conductor and the wires of the conductor are not severed in the course of the method.

In some embodiments, the internal side and/or the external side of the electrode are micro-structured or coated before and/or after being connected to the conductor.

The micro-structuring can effect a lower impedance or improve the electrical contact between conductor and electrode or the contact with the body of a living being. The surface can be structured, for example, by means of a laser. In one embodiment, the surface is enlarged by roughening the surface. This can take place with a variety of methods, for example by means of a laser.

A coating can effect a lower impedance or improve the electrical contact between conductor and electrode or the contact with the body of a living being. TiN, Ir, $IrO_x$, Pt or conductive polymers, for example conductive polymers based on thiophene, such as, for example, poly-3,4-ethylenedioxythiophene (PEDOT) or the conductive polymers described in WO/2015/031265, can be used for the coating. A coating can be effected, for example, by means of PVD, CVD or electrochemical deposition.

In some embodiments, the surface structure of the electrode is not impaired or impaired a little by the attachment. This is the case if no or a particular gentle clamping connection is used. This is advantageous in the embodiments specified above in that functions and/or effects generated by the coating and/or structuring are not being impaired.

In a further aspect, one embodiment provides a system for reception and/or emission of an electrical signal from and/or into the human or animal body that can be produced or is produced through a method according to the embodiments described herein. The system is characterised by an improved contacting of conductor and electrode and, if applicable, the further advantages described herein.

An electrode can be produced as follows, for example:
(1) Initially, drawing a metal tube from a suitable material, for example Pt, Ir, Ta, Pd, Ti, Fe, Au, Mo, Nb, W, Ni, Ti or alloys thereof, for example PtIr10, PtIr20, MP35, 316L, 301 or 304, as described herein, with the desired target diameter. (2) Then, ring electrodes of target length can be severed from the drawn tube, for example by means of laser cutting methods, spark erosion or mechanical cutting. (3) The slit can be generated, for example, by means of laser cutting, mechanical cutting, spark erosion or metal cutting methods. By this means, for example a ring electrode with a slit through the ring wall can be produced.

The procedural steps described above of (2) cutting (severing) ring electrodes from the drawn metal tube and (3) cutting the slit can be implemented in any order, i.e. step (2) can be performed before or after step (3).

Alternatively, the electrode according to one embodiment can be produced through powder metallurgical procedures such as metal powder injection moulding, recasting methods or additive procedures, e.g. selective laser melting, direct metal-laser sintering, laser deposit welding, electron-beam melting, lithography (also called bottom-up or build-up procedures).

The way and manner of the production of the electrode described above is a continuous procedure that does not require any specifically adapted tool. Accordingly, for example electrodes of different lengths can be produced without adapting a tool specifically to the length and/or without producing an adapted tool.

An electrical conductor can be produced from a plastic-insulated metal wire, as is known in this technical field. As a matter of principle, any known suitable method can be used for this purpose. If applicable, multiple insulated conductors of this type can be stranded to each other or bundled in other manner in order to arrange as many conductors as possible within the smallest possible total diameter. In one embodiment, the insulated conductors are arranged in a coil shape about a hollow space (also called coil structure).

A further aspect of one embodiment relates to a diagnostic method in or on the body of a living being, comprising the reception of an electrical signal by means of the system described herein.

A further aspect of one embodiment relates to the use of the system described herein in a diagnostic method in or on the body of a living being, comprising the reception of an electrical signal by means of the system.

A further aspect of one embodiment relates to a therapeutic method in or on the body of a living being, comprising the emission of an electrical signal by means of the system described herein.

A further aspect of one embodiment relates to the use of the system described herein in a therapeutic method in or on the body of a living being, comprising the emission of an electrical signal by means of the system.

The therapeutic method can include the emission of an electrical signal to nerve cells or muscle cells in the area of an organ, for example heart, muscle, stomach or brain.

The diagnostic method can include the reception of an electrical signal from nerve cells or muscle cells in the area of an organ, for example heart, muscle or brain.

Examples

One embodiment is illustrated further in the following based on examples, though these may not be construed such as to limit embodiments in any way or form. It will be obvious to a person skilled in the art that, in place of the features described herein, other equivalent means can be used in like manner.

Figure 1:
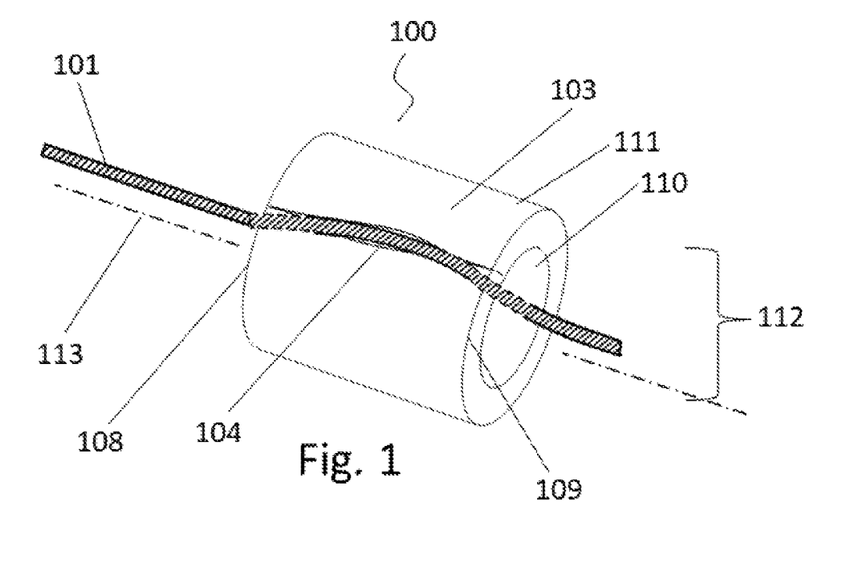
FIG. 1 illustrates a system according to one embodiment, in which an electrode and a conductor are electrically connected to each other.

FIG. 1 illustrates a system 100 according to the present embodiment in exemplary manner. The system is set up to emit an electrical signal to the human or animal body or to receive an electrical signal from the human or animal body, or both. The system includes an electrical conductor 101, which is arranged along a longitudinal axis 113 of a channel 112. The channel 112 forms the internal space of the electrode 103. The electrical conductor 101 is connected to an electrode 103. The electrode 103 includes an internal side 110 and an external side 111 and is, for example, designed to be essentially cylindrical, i.e. sleeve-shaped (also called ring electrode). The electrical conductor 101 can be arranged, in part, within the channel 112. At least a part of the electrical conductor 101 is arranged within a slit 104 in the electrode 103 in order to establish an electrical connection between the conductor 101 and the electrode 103. The slit 104 extends from an internal side 110 of the electrode 103 to an external side 111 of the electrode 103 such that the slit 104 interrupts the external wall of the electrode. The slit 104 can interrupt the external wall of the electrode 103 partially or completely. The slit 104 can extend from a first external edge 108 of the electrode 103 to a second external edge 109 of the electrode 103. The conductor 101 extends without interruption along the entire area of the electrode 103. This means that the conductor 101 is arranged continuously, i.e. includes no interruptions in the vicinity of the electrode 103.

The conductor 101 is being connected to the electrode 103 within the slit 104 in directly firmly-bonded and/or force-locking manner. The connection keeps the conductor 101 durably safe in the opening 104 and provides for a stable and error-free electric connection between conductor 101 and electrode 103. In one embodiment, the connection is designed appropriately such that the opening slit 104 is hermetically closed, i.e. is liquid-tight, for example. This can be attained, for example, through a welded connection, but a connection by brazing or soft soldering is feasible just as well. The connection can also be established by clamping, for example crimping, clamping with pliers or swaging (also called drop forging) of the conductor 101 in the slit 104. The connection can also be attained through a combination of welding and clamping. In one embodiment, the connection contains no further elements other than the conductor 101, the electrode 103, and a welded connection. In one embodiment, the conductor 101 is connected to the electrode 103 exclusively through a welded connection.

Figure 2:
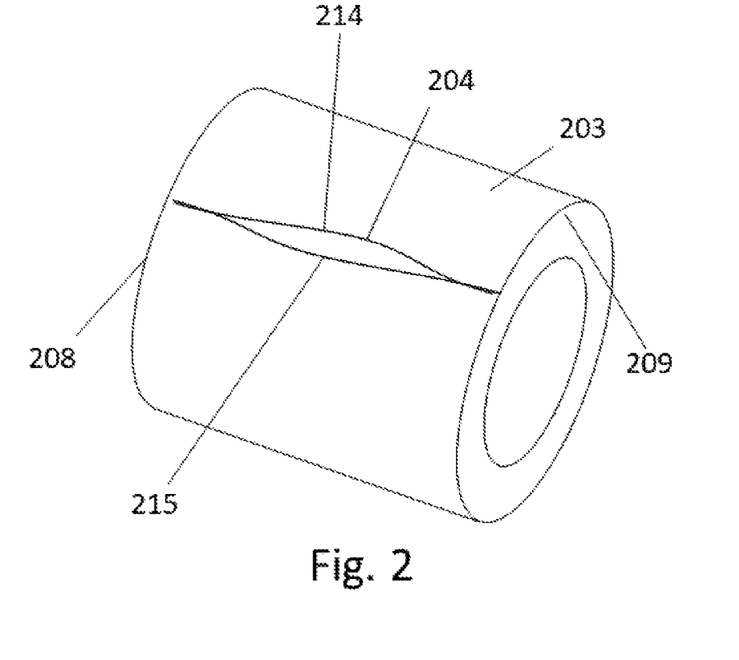
FIG. 2 illustrates a possible design of a slit in a ring-shaped electrode in exemplary manner.

FIG. 2 illustrates an exemplary depiction of an electrode 203 with a slit 204 that extends from a first external edge 208 of the electrode 203 to a second external edge 209 of the electrode 203. The slit 204 forms an opening in the electrode 203 that is wider in the central part than in the area of the first external edge 208 and second external edge 209. Accordingly, the slit 204 has an essentially elliptical shape. The slit 204 is set up appropriately such as to accommodate a conductor (in FIG. 2) in the central part of the slit 204.

FIG. 3A to FIG. 3D illustrate individual steps of the method according to one embodiment.

Figure 3A:
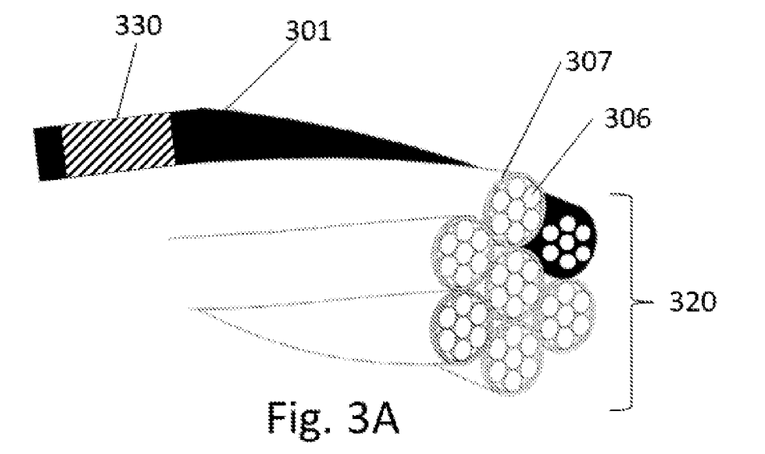
FIG. 3A illustrates the partial ablation of the insulating layer of the conductor in order to expose one or more wires and enable a contacting.

FIG. 3A illustrates a conductor bundle 320 that includes multiple conductors 301 that are stranded to each other into a coil shape. Each of the conductors 301 includes multiple wires 306 on the inside of the conductor 301. The conductor 301 includes an insulation 307 that surrounds the conductor 301. The insulation surrounds all wires 306 of the conductor 301. At the site, at which the conductor 301 is to be connected to an electrode, part of the insulation 307 of the conductor is removed in order to form an exposed section 330. In this section 330, a single wire 306 can be guided out of the conductor. Just as well, multiple wires 306, for example the entire conductive part of the conductor 301, can be guided out of the conductor 301 such that these wires 306, for example all wires 306 of the conductor 301, extend out of the inside of the conductor 301 outwards beyond the insulation 307.

Figure 3B:
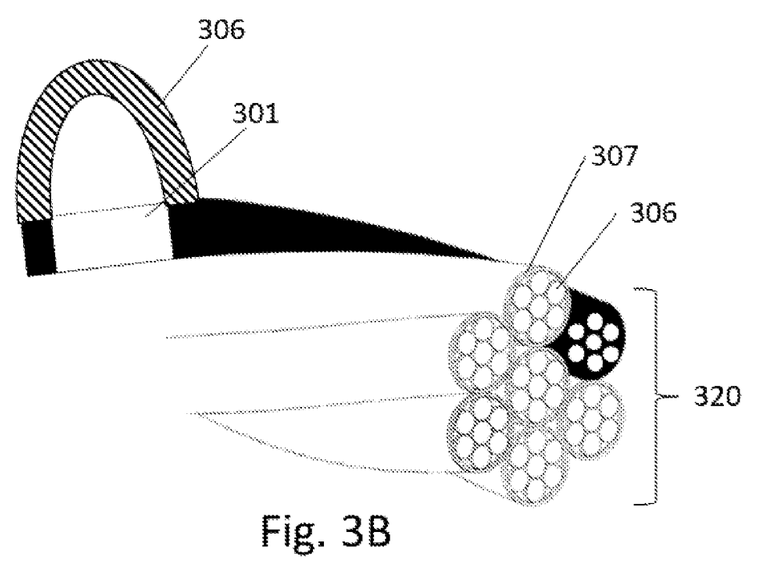
FIG. 3B illustrates a schematic depiction of a conductor being lifted in order to enable a contacting within the slit.

FIG. 3B illustrates a conductor bundle 320 that includes multiple conductors 301. Each of the conductors 301 includes multiple wires 306 and an insulation 307. One of the wires 306 is guided out of the conductor 301 in the exposed section. Just as well, multiple wires 306, for example the entire conductive part of the conductor 301, can be guided out of the conductor 301.

Figure 3C:
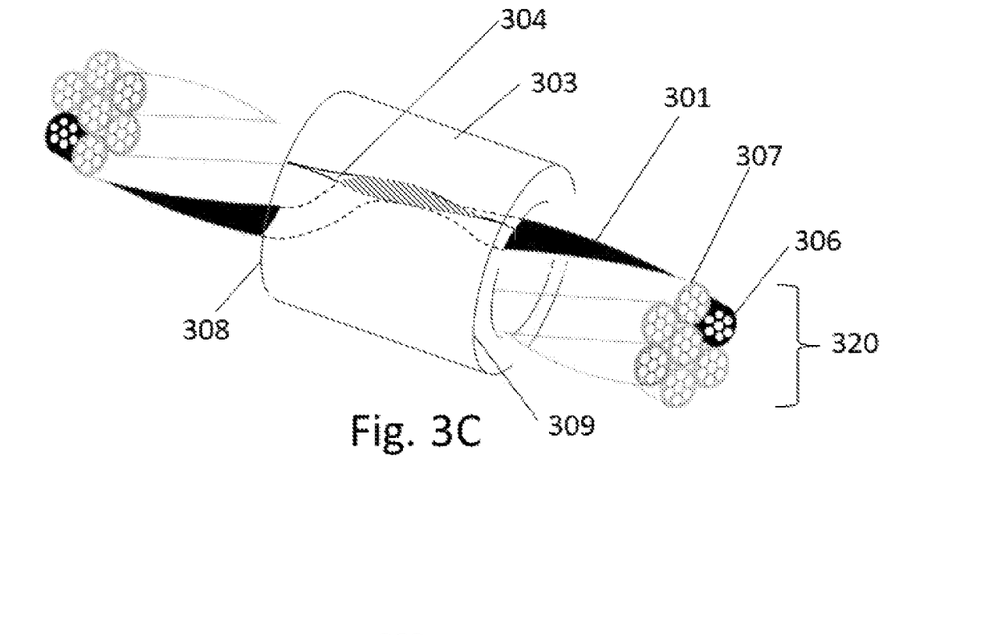
FIG. 3C illustrates the conductor being arranged within the slit for connecting it to the electrode.

FIG. 3C illustrates the part of the wire 306 that has been guided out of the conductor 301 being guided into the slit 304. This can take place, for example, by laterally shifting the electrode 303 along the conductor bundle 320 until the wire 306 projecting from the conductor 301 protrudes into the slit 304 after the electrode 303 has been guided onto the conductor bundle 320 such that the electrode 303 surrounds the conductor bundle 320. Just as well, multiple wires 306, for example the entire conductive part of the conductor 301, can be guided out of the conductor 301 and guided into the slit 304.

The slit 304 can be pushed together such that the conductor 301 arranged in the slit 304 is clamped and thus becomes connected to the electrode 303 in force-locking manner.

Figure 3D:
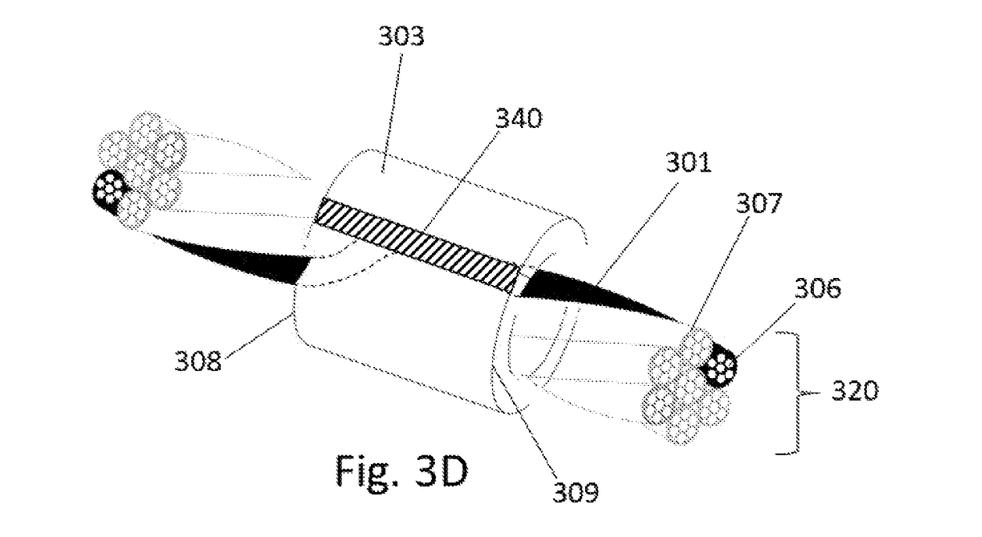
FIG. 3D illustrates the conductor being attached in the slit by means of a firmly-bonded connection.

FIG. 3D illustrates the wire 306 being connected to the electrode 303 by welding the wire 306 to the electrode 303 within the slit 304 in order to form a welded seam 340. By this means, the conductor 301 is connected to the electrode 303 within the slit 304 in direct, durable and electrically conductive manner.

The connection can be effected by means of a force-locking connection, for example by compressing the opening in order to hold the wire 306 in a force-locking manner. A combination of force-locking and firmly-bonded connection methods can be used just as well. In one embodiment, the wire 306 is being welded within the opening such that the molten material of the wire 306 and/or the material of the electrode partially or completely fills the intervening spaces between the wire 306 and the electrode in the area of the opening such that a stable electrical and mechanically durable connection between the wire 306 and the electrode can be formed. In one embodiment, the material molten during the welding covers the entire external side of the opening. Also in one embodiment, the material molten during the welding covers the external edges of the slit in order to prevent sharp edges on the external side of the system.

The electrode can be micro-structured just as well, for example by means of a laser, as described elsewhere herein. The procedural step can take place before or after contacting the electrode to the conductor. The micro-structuring can, for example, increase the surface roughness in order to facilitate a better connection to other materials. The electrode can just as well be coated with a further material, as described in detail elsewhere herein. The procedural step can take place before or after contacting the electrode to the conductor. In some embodiments, the electrode is first being micro-structured and then coated. A micro-structuring of the coating can take place just as well. In one embodiment, the contacting of the conductor to the electrode takes place exclusively through a welded connection, and subsequently the electrode is being micro-structured and/or coated. The coating can improve the reception or emission of an electrical signal or the biocompatibility.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A system for reception or emission of an electrical signal from or into a human or animal body, comprising:
at least one insulated electrical conductor;
a sleeve-shaped electrode that is electrically connected to the at least one insulated electrical conductor and comprises an internal side, an external side, and a channel, wherein the channel defines a longitudinal axis along which the at least one insulated conductor is arranged;
wherein the at least one insulated conductor extends without interruption along an entire length of the electrode along the longitudinal axis and extends beyond the length of the electrode in both directions along the longitudinal axis and without any termination of the insulated conductor at the electrode, and the electrode further comprises a slit that extends from the internal side to the external side of the electrode and in which the at least one insulated conductor is arranged in the slit extending from the channel into the slit and returning back into the channel from the slit and such that the electrode forms a direct durable mechanical and electrical connection to the at least one insulated conductor.

2. The system according to claim 1, wherein the at least one insulated conductor is connected to the electrode inside the slit directly in force-locking and/or directly in firmly-bonded manner.

3. The system according to claim 1, wherein the slit extends continuously from the internal side to the external side of the electrode.

4. The system according to claim 1, wherein, other than the direct connection between the at least one insulated conductor and the electrode, there is no further component present that connects the at least one insulated conductor to the electrode.

5. The system according to claim 1, wherein the slit extends along the longitudinal axis from a first external edge of the electrode to a second external edge of the electrode.

6. The system according to claim 5, wherein the electrode comprises, each on the first external edge of the electrode and on the second external edge of the electrode, a direct connection of two opposite surfaces of the slit.

7. The system according to claim 1, wherein the slit comprises an essentially elliptical recess that is arranged in the center of the slit and is configured to form a direct force-locking and/or firmly-bonded connection between the at least one insulated conductor and the electrode.

8. The system according to claim 1, wherein the insulation of the at least one insulated conductor comprises an exposed section at a position where the electrode forms a direct durable mechanical and electrical connection to the at least one insulated conductor.

9. The system according to claim 1, wherein the electrode is coated and/or micro-structured.

10. The system according to claim 1, comprising a multitude of electrodes and a multitude of conductors, wherein each individual one of the multitude of electrodes is connected to exactly one of the multitude of conductors in order to render the electrodes electrically addressable independent of each other.

11. An electrical medical device comprising a system according to claim 1 and configured as a lead, pulse generator, cardiac pacemaker, cardiac resynchronisation device, sensor or stimulator.

12. A method for electrical contacting of an insulated electrical conductor, comprising the following steps:
  a. providing the insulated electrical conductor and a sleeve-shaped electrode that comprises an internal side, an external side, a channel, and a slit that extends from the internal side to the external side of the electrode;
  b. exposing the insulation in a section of the insulated electrical conductor at which the insulated electrical conductor is to be connected to the electrode;
  c. attaching the electrode to the insulated electrical conductor such that the insulated electrical conductor becomes arranged along the longitudinal axis of the channel;
  d. arranging the insulated electrical conductor in the slit such that the insulated electrical conductor can be connected to the electrode;
  e. connecting the insulated electrical conductor to the electrode, wherein a direct force-locking and/or firmly-bonded electrical connection between the insulated electrical conductor and the electrode is formed within the slit, and wherein the insulated conductor extends from the channel into the slit and returns back into the channel from the slit without interruption along an entire area length of the electrode and extends beyond the length of the electrode in both directions along the longitudinal axis and without any termination of the insulated conductor at the electrode.

13. The method according to claim 12, wherein the external side of the electrode is being micro-structured or coated before and/or after connection to the insulated electrical conductor.

14. A system for emission of an electrical signal to the human or animal body, that is produced through a method according to claim 12.

* * * * *